United States Patent [19]

Messenger et al.

[11] Patent Number: 4,970,171
[45] Date of Patent: Nov. 13, 1990

[54] DENATURANT REAGENTS FOR CONVENIENT DETERMINATION OF HEMOGLOBIN DERIVATIVES IN BLOOD

[75] Inventors: Lowry Messenger, Granger; Frances M. Yeager, Middlebury; Kin F. Yip, Elkhart, all of Ind.

[73] Assignee: Miles Inc., Elkhart, Ind.

[21] Appl. No.: 118,476

[22] Filed: Nov. 9, 1987

[51] Int. Cl.$^5$ ............................................. G01N 33/72
[52] U.S. Cl. ........................................ 436/66; 436/67; 436/17; 436/501; 436/522; 436/808
[58] Field of Search ................. 436/66, 67, 534, 501, 436/522, 17, 164, 805, 808; 422/68, 55

[56] References Cited

U.S. PATENT DOCUMENTS

| | | | |
|---|---|---|---|
| 4,255,385 | 3/1981 | Stroupe et al. | 436/67 |
| 4,407,961 | 10/1983 | Sanders et al. | 436/67 |
| 4,438,204 | 3/1984 | Deeg et al. | 436/67 |
| 4,647,654 | 3/1987 | Knowles et al. | 530/326 |
| 4,649,122 | 3/1987 | Lee | 436/57 |
| 4,658,022 | 4/1987 | Knowles et al. | 436/87 |

OTHER PUBLICATIONS

Kampen et al "Determination of Hemoglobin and its Derivatives", Advances in Clinical Chemistry vol. 8, (1965) pp. 141–187.
NCCLS Proposed Standard: PSH–15; Reference Procedure for the Determination of Hemoglobin in Blood.
Habeeb, "Determination of Free Amino Groups in Proteins by Trinitrobenzenesulfonic Acid", Anal. Biochem 14, 328–336 (1966).
Grassetti et al, "Determination of Sulfhydryl Groups with 2,2'or 4,4'-Dithiodipyridine", Arch of Biochem & Biophysics 119, 41–49 (1967).
Alpert "Cation-Exchange HPLC Chromatography of Proteins on Poly(Aspartic Acid)-Silica", Jo of Chromatography 226 (1983) 23–37.

Primary Examiner—Robert J. Warden
Assistant Examiner—Lyle Alfandary-Alexander
Attorney, Agent, or Firm—Andrew L. Klawitter

[57] ABSTRACT

An analytical method for determining the relative amount of a particular hemoglobin derivative, e.g., glycated hemoglobin, in a blood sample wherein the amounts of both total hemoglobin and the hemoglobin derivative are measured and related mathematically, e.g., as a percentage. The blood sample is treated with the combination of a thiocyanate salt and an oxidant to denature the hemoglobin in the sample and to convert hemoglobin to met-hemoglobin. Met-hemoglobin is measured spectrophotometrically to give the amount of total hemoglobin present, and the denatured hemoglobin derivative can be distinguished and measured by immunoassay. The presence of the oxidant in the denaturant solution has been found to increase the rate of enaturation of hemoglobin thereby reducing the overall assay time and improving the reliability of the determination.

19 Claims, 1 Drawing Sheet

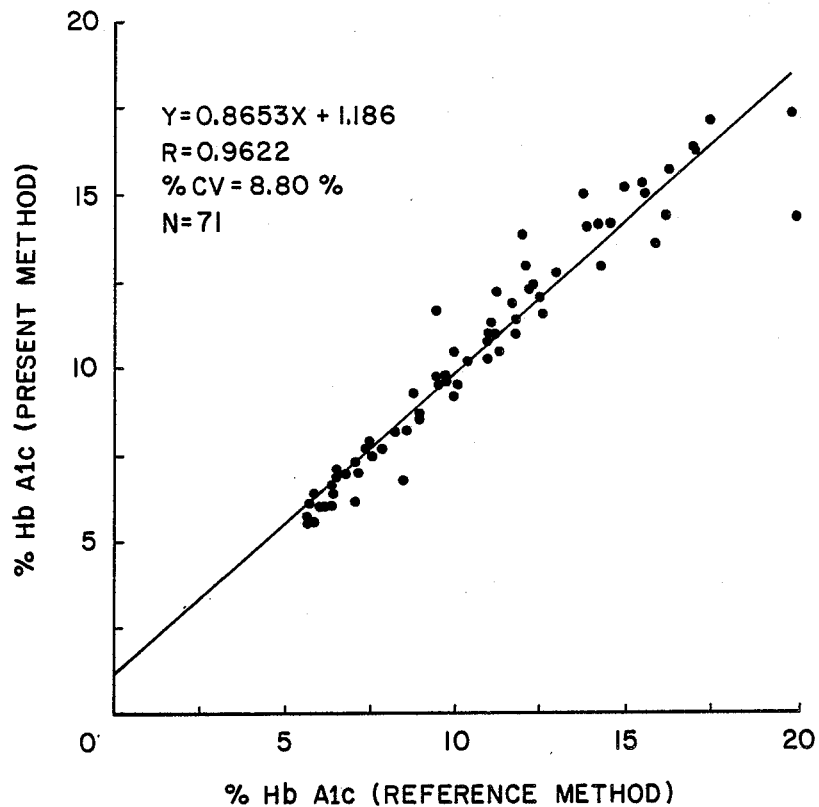

DENATURANT REAGENTS FOR CONVENIENT DETERMINATION OF HEMOGLOBIN DERIVATIVES IN BLOOD

BACKGROUND OF THE INVENTION

This invention relates to methods for determining the relative amount of a particular hemoglobin derivative in blood samples. More particularly, the invention concerns the determination of hemoglobin derivatives, such as glycated hemoglobin, which requires the separate measurement of total hemoglobin as well as the measurement of the hemoglobin derivative in order to determine the proportion or percentage of the derivatized hemoglobin in the blood.

The determination of the relative amount of hemoglobin that exists in the bloodstream in a particular derivative form generated by in vivo processes is of importance in a variety of medical situations. Of particular significance is the measurement of glycated hemoglobins (sometimes referred to as glycosylated hemoglobins). The measurement of glycated hemoglobin to assess the long-term blood glucose control in diabetes mellitus is being used with increasing frequency. The most important of the glycated hemoglobins in diabetes management is the derivative commonly known as hemoglobin Alc. This hemoglobin derivative is produced in vivo by the nonenzymatic reaction of glucose with hemoglobin. Glucose becomes covalently attached in a rearranged form to the amino-terminal valine residue of the beta-chain in native hemoglobin. Normal individuals have between about 3 and 6 percent of their total hemoglobin in the Alc form, while an uncontrolled diabetic individual could have as much as 3 to 4-fold higher levels of this hemoglobin derivative in the blood stream.

A variety of methods have been developed for the purpose of determining glycated hemoglobins. The conventional methods are based on diverse techniques such as cation exchange chromatography, affinity chromatography, electrophoresis, and dye complexation (hydroxyfurfural/thiobarbituric acid). These techniques are well known to be tedious, complex, requiring special technical skills, and to suffer from imprecision and nonspecificity. Very recently, monoclonal antibodies specific for the glycated N-terminal peptide residue in hemoglobin Alc have been developed which enable the performance of immunoassays to determine this hemoglobin derivative (see U.S. Pat. No. 4,647,654).

The immunoassay determination of hemoglobin Alc using monoclonal antibodies is highly specific and the procedure is significantly less tedious and complex than the prior art methods. Nevertheless, the optimal hemoglobin Alc immunoassays require that the blood sample be subject to denaturing conditions in order that the glycated N-terminal peptide residue becomes available for antibody binding (see U.S. Pat. No. 4,658,022). Typical denaturing conditions have thus far been 3 molar guanidine-HCl with heating to 56° C. for 15 minutes or more.

A further limitation of the prior art techniques, including the immunoassay approach, is the requirement that a total hemoglobin measurement be conducted with each determination in order that the glycated hemoglobin level can be expressed meaningfully as a percentage. This only adds to the total time and expense of performing the assay.

SUMMARY OF THE INVENTION

It has now been found that a fairly simple, rapid, and precise assay for a particular hemoglobin derivative such as glycated hemoglobin can be performed by treating a blood sample with denaturant reagents comprising (i) a thiocyanate salt to denature the hemoglobin in the sample, and (ii) an oxidant capable of converting the hemoglobin to the met-hemoglobin form, and then assaying the treated sample for total met-hemoglobin and assaying the same or another portion of the sample for the denatured form of the hemoglobin derivative of interest. The two assay results are then related in any desired mathematical manner, e.g., as a percentage, to provide a quantitative measure of the relative amount of the hemoglobin derivative in the sample.

Met-hemoglobin is conveniently determined by measuring its characteristic absorbance at 540 nanometers (nm). The denatured form of the hemoglobin derivative of interest can be simply and specifically determined by immunoassay. A particularly useful immunoassay technique is based on particle agglutination inhibition which can be designed to be read by turbidimetry at any convenient wavelength, even the same wavelength as the met-hemoglobin measurement, i.e., 540 nm. Thus, the present invention makes possible the determination of percent hemoglobin derivative with total hemoglobin and hemoglobin derivative measurements taken with a simple spectrophotometer and, with appropriate blanks and optimization, at a single wavelentgh.

The presence of an oxidant which converts native hemoglobin ($Fe^{+2}$) in blood to the ($Fe^{+3}$met-hemoglobin form has been found to act synergistically with the thiocyanate denaturant to increase the rate of the denaturation of the sample hemoglobin for the immunoassay portion of the test. In the absence of oxidant, the thiocyanate denaturation at room temperature requires up to about 7 minutes to attain a reproducible level of essentially complete denaturation. When an effective amount of oxidant is present, essentially complete denaturation can be achieved in under 3 minutes, and in the case of the preferred oxidant, ferricyanide, can be achieved in under one minute at room temperature. The combination of oxidant and thiocyanate also makes possible the performance of the total hemoglobin and hemoglobin derivative assays on the same test sample.

The present invention therefore has significantly reduced the overall assay time and has facilitated the performance of a rapid, simple, and precise met-hemoglobin/immunoassay method for quantitating the relative amount of a hemoglobin derivative such as hemoglobin Alc in a blood sample.

BRIEF DESCRIPTION OF THE DRAWING

The drawing is a graph depicting the results of a correlation study between the present analytical method and a conventional affinity chromatography method in determining hemoglobin Alc in clinical specimens.

DESCRIPTION OF THE PREFERRED EMBODIMENTS

The combination of a thiocyanate salt and oxidant as denaturant reagents provides a means of rapidly and reproducibly converting essentially all of the hemoglobin in a blood sample into a denatured thiocyan-met-hemoglobin form. The resulting thiocyan-met-hemoglobin serves as the basis for measuring total sample hemoglobin, with the denatured form of the particular hemoglobin derivative of interest serving as the analyte in an immunoassay for such denatured species. The immunoassay is preferably based on the specific affinity of a monoclonal antibody for the denatured hemoglobin derivative of interst.

The thiocyanate salt can be selected from any salt form that upon ionization provides thiocyanate anion (SCN$^-$) effective to denature the hemoglobin derivative for detection in the assay. The countercation will be selected to minimize or eliminate any possible interferences with the total and derivatized hemoglobin assays. Ammonium, potassium, and sodium thiocyanate are useful salts for the purposes of the present invention. The thiocyanate salt solution will be added to the blood sample in sufficient amount to give an effective denaturing concentration in the mixture. In the normal case, a concentration of between about 0.5 and about 6.0 molar, more usually between about 1.5 and about 3.5 molar, in the denaturation mixture will be used. Increasing denaturant concentrations result in faster denaturation. Also, elevation of temperature generally increases the rate of denaturation. Preferred conditions are denaturation at room temperature in the presence of thiocyanate at a concentration of about 3 molar or greater. In cases where the concentration of thiocyanate in the denaturation mixture is at a level that could affect the performance of the immunoassay for the hemoglobin derivative, e.g., at concentrations above 1.5-2.0 molar, the mixture will be diluted appropriately.

The oxidant can be selected from essentially any inorganic or organic oxidizing agent of sufficient electrochemical potential to convert the native hemoglobin ferrous ion to its ferric met-hemoglobin form. Of course, an oxidant candidate selected by its oxidation potential will be tested in the assay system to assure that it will not interfere significantly with the total and derivative hemoglobin assays. A variety of oxidants are known in the literature to be effective in converting hemoglobin to its met-hemoglobin form—see Advances in Clinical Chemistry 8:142-185 (1965). Oxidants that qualify based on oxidation potential include ferricyanide, iodate, chlorate, bromate, chromate, mercuric chloride, ceric and thallium ions, hypochlorite, periodate, iodide, hydroxyamine, bromosuccimide, chlorosuccimide, chloroamine, and peroxide. The degree of enhancement of the denaturation kinetics, yielding a reduced time for essentially complete denaturation, will of course vary according to the oxidant selected. Empirical testing can be readily performed to enable selection of an oxidant that, in combination with the thiocyanate, provides sufficiently rapid denaturation.

Essentially complete denaturation shall be understood in the present context to mean the point at which the denaturation of hemoglobin in the blood sample provides substantially the maximum amount of the denatured hemoglobin derivative that can be detected using the selected immunoassay. Therefore, the concept of complete denaturation does not intend necessarily the complete disruption of all tertiary and secondary structure of the hemoglobin protein, but rather maximum exposure of the epitope of the hemoglobin derivative detected by the selected immunoassay means. Normally, the immunoassay is based on monoclonal antibody specificity for a unique epitope that characterizes the hemoglobin derivative. Thus, essentially complete denaturation of hemoglobin in a sample would mean that essentially all of such hemoglobin has been denatured sufficiently so as to be fully detectable in the assay. One determines the time it takes to reach essentially complete denaturation under given denaturing conditions by performing the hemoglobin derivative immunoassay at prescribed time intervals and observing the point at which the assay response curve approaches a plateau.

The oxidant will be added in excess amounts, for example, in 5-fold excess of the amount of heme normally present in the sample. Amounts up to 20-fold excess can be used advantageously. Appropriate amounts for particular assays can be determined by the worker in the field.

In the absence of oxidant, thiocyanate denaturation at room temperature requires up to 7 minutes to reach essentially complete denaturation. Oxidants which have been found to decrease this denaturation time without substantially interfering with the immunoassay include ferricyanide, iodate, chlorate, chromate, and nitrite. Chlorate and nitrite have, in particular, been found to reduce the denaturation time to under 3 minutes, with ferricyanide yielding the best results with essentially complete denaturation in less than one minute at room temperature with thiocyanate concentrations of about 3 molar or greater.

A major advantage of using the thiocyanate/oxidant denaturant is the ability to attain rapid denaturation at room temperature. However, if considered desirable, denaturation can be accelerated further by elevating the temperature. Further, the use of a combination of different oxidants with thiocyanate is also contemplated by the present method.

The thiocyanate/oxidant denaturant pair can be mixed with the blood sample stepwise or, as would be preferred, simultaneously. Normally, a denaturant reagent solution of the thiocyante and oxidant is prepared and mixed directly with the blood sample. For reasons of stability, the denaturant reagent solution will oftentimes be prepared only immediately prior to its use in the assay. However, where stability will allow or where stabilizing agents or construction of the device are used which permit the thiocyanate salt and oxidant to be together, the denaturant reagent solution can be stored and/or packaged over prolonged time periods. The denaturant components can be in a dry form and mixed or otherwise associated so as to form the reagent solution upon rehydration with test sample and/or a diluent or buffer.

It is contemplated that the present method applies to the assay of any hemoglobin derivative in blood which is detected in its denatured form by immunoassay. Such hemoglobin derivatives, include without limitation, acetaldehyde-hemoglobin adducts associated with alcohol abuse, urea-hemoglobin adducts present in the blood of uremic patients, aspirin-hemoglobin complexes, and particularly the family of glycated hemoglobins formed by nonenzymatic reaction of glucose with reactive amine groups on the hemoglobin protein. The present invention is especially applicable to the determination of hemoglobin Alc as defined above.

The treated, denatured blood sample is separately assayed for total met-hemoglobin and for the hemoglobin derivative of interest, followed by a mathematical correlation of the results to give a measure of the relative amount of the blood hemoglobin that is in the derivatized form of interest. Total met-hemoglobin can be measured in any conventional manner such as the Drabkins' procedure (National Commission for Clinical Laboratory Standards of the U.S., Proposed Standard PSH-15). A most convenient method for measuring total met-hemoglobin is by measuring its absorbance in solution at a characteristic wavelength, e.g., 540 nm.

The determination of the hemoglobin derivative will normally be performed by immunoassay. As described in the aforementioned U.S. Pat. Nos. 4,647,654 and 4,658,022, monoclonal antibodies can be developed which bind specifically to the epitope that characterizes the hemoglobin derivative, e.g., hemoglobin A1c, in the denatured protein. The particular immunoassay technique and format, as well as the labeling approach and detection signal generated, is not critical to the present invention. In principle, nonradioisotopic methods are preferred, such as those based on the use of enzyme labels (ELISA) and the like.

A method that is particularly useful because it can be performed without a separation step and provides a measurable absorbance change related to analyte concentration is particle agglutination inhibition immunoassay. Such an assay is based on the specific interaction of an antibody particle reagent and an agglutinator reagent. The antibody particle reagent comprises the antibody, or a fragment thereof, bound to a water suspensible particle (e.g., a polystyrene or other latex). The agglutinator comprises a plurality of epitopic binding sites for the antibody reagent. In the absence of analyte, the antibody particle and agglutinator bind to one another to form a light scattering complex that is readily quantitated by turbidimetric measurement. In the presence of increasing amounts of analyte, the turbidity of the solution decreases as antibody particles become bound to the analyte and cannot bind to the agglutinator. The agglutinator can conveniently comprise a polymer backbone to which are attached a number of organic moieties, e.g., peptide residues, which define the epitope that characterizes the hemoglobin derivative of interest. For example, for hemoglobin A1c determinations, the epitopes can comprise glycated peptide residues of a few amino acid units corresponding to the sequence of the glycated N-terminal residue in hemoglobin A1c.

The respective total met-hemoglobin and derivative hemoglobin assays can be performed on the same or different portions of the treated blood sample. In the latter case, a first volume of the treated sample is directly assayed for met-hemoglobin, usually after making an appropriate dilution in buffer, and a second volume is assayed for the denatured hemoglobin derivative as described above. It is also possible to conduct both assays in series on the same treated sample volume such as by making an appropriate dilution of the treated sample, assaying for thiocyan-met-hemoglobin, and then either adding the reagents of the immunoassay system or adding the solution to such reagents.

Using the particle agglutination inhibition immunoassay approach, a number of possible assay protocols can be applied to the denaturant mixture formed by mixing the blood sample with the denaturant of the present invention.

One protocol involves dilution of a portion of the denaturant mixture with buffer or water for the hemoglobin measurement. A second portion of the denaturant mixture is mixed with antibody-particle reagent and the agglutinator for the immunoassay, e.g., performed at 540 nm either with end-point or rate measurement (at room temperature or 37° C.).

Another protocol involves dilution of the denaturant mixture with a solution containing the agglutinator reagent. Hemoglobin is measured at 550 nm in this mixture. Then, the antibody-particle reagent is added to start the immunoassay, e.g., rate measurement at 600 nm.

In another protocol, the denaturant mixture is diluted with buffer and hemoglobin measured. The diluted mixture is then mixed with the antibody-particle and agglutinator reagents and the immunoassay measured at 540 nm by rate measurement.

Yet another protocol involves measurement of hemoglobin directly in the denaturant mixture. The antibody-particle and agglutinator reagents in dry form are then dissolved into the denaturant mixture, simultaneously or in sequence (with or without an intervening blank reading), and the immunoassay performed as above.

A particularly useful assay protocol is described in the Examples below.

The present invention provides a test system for performing the assay method, comprising the thiocyanate salt, the oxidant, and the immunoassay reagents for the determination of the denatured hemoglobin derivative. Preferably, the immunoassay reagents are those of the particle agglutination inhibition system described above. Met-hemoglobin reagents can also be included, however, the preferred absorbance method for determining met-hemoglobin will of course not require any reagents, other than possibly distilled water or a buffer diluent. The test system can be in any convenient form, and will normally be in the form of a test kit comprising a packaged combination of containers holding the components of the test system.

The invention will now be illustrated, but is not intended to be limited, by the following Examples.

EXAMPLES

1. Preparation of Reagents

A. Antibody-Latex Reagent:
Materials Required:
   2% latex suspension [0.085μ diameter polystyrene latex, Seragen, Indianapolis, IN, U.S.A. ]
   Antibody solution [Monoclonal antibody prepared as described in U.S. Pat. No. 4,647,654, purified from ascites fluid by protein A affinity chromatography (BioRad Laboratories, Richmond, CA, U.S.A.)]
   10 mM glycine buffer, 0.02% azide, pH 9.3 100 mM NaCl The antibody coating is done at a latex concentration of 0.5% and the antibody is normally used in a final concentration of 1 mg/mL in the coating reaction. An antibody solution at 2× concentration is prepared by diluting the required amount of antibody into a 10 mM glycine buffer with added NaCl to give the final conductivity desired (between 0.5 and 1.8 mmho). The 2% latex is diluted to 2× concentration (or 1%) by mixing with an equal volume of the 10 mM glycine buffer. The reaction is initiated by pouring the latex suspension into a vessel containing the antibody solution. The antibody solution is mixed with a magnetic stir bar when the latex is added. All solutions are at room temperature. The mixing is continued overnight (at least 15 hours) taking care to insulate the vessel so that heating from the magnetic stir plate does not occur. This can be accomplished by suspending the vessel above the stir plate leaving about an inch air space for insulation.

After the 15 hours mixing, the resulting suspension is divided equally into polypropylene centrifuge tubes (approximately 10 mL per tube) for a Sorvall SS-34 rotor [Dupont, Wilmington, DE, U.S.A.]. The suspension is centrifuged at 15,000 rpm (2700×g) for 60 minutes. The supernatant is decanted. The pellet is washed two times with 10 mM glycine buffer containing the desired overcoating protein [typically 1% protease free bovine serum albumin (BSA-pf) obtained from Miles Inc., Elkhart, IN, U.S.A.]. To wash the pellet, a volume of wash solution equal to the original volume in the tube is added. The pellet is resuspended by vigorous vortexing and short-term sonication (10–15 seconds at a time). After the initial resuspension, the Ab-latex is allowed to stand at room temperature for one hour before recentrifuging. After the initial resuspension and centrifuging, subsequent resuspensions are centrifuged immediately once the pellet is completely dispersed. After the second wash, the pellets are resuspended in a volume equal to the initial reaction volume. The suspension is filtered through a $0.8\mu$ filter and stored at 5° C.

The concentration is determined by measuring the absorbance at 546 nm of the original supernatant, the supernatant from the first and second washings, and a 100× dilution of the final sample. The sum of these absorbances is assumed to be 100% or equal to 0.5% latex. The absorbance of the final sample is divided by the sum of the absorbances used to calculate 100%. The absorbance of the 100× dilution of the final sample is multiplied by 100 to generate an absorbance for the final sample.

| Example: | |
|---|---|
| Sample | $A_{546}$ |
| Supernatant | 0.044 |
| First Wash | 0.034 |
| Second Wash | 0.021 |
| Final (100 × dil) | 0.051 × 100 = 5.1 |
| 100% (or 0.5% latex) = 5.10 + 0.044 + 0.034 + 0.021 = 5.199 | |
| Latex concentration of final sample = (5.1/5.199) × 0.5% = 0.49% | |

B. Agglutinator Reagent:

Poly(aspartic acid) was prepared according to the procedure of Alpert J. Chromatography 266:23(1983). Aminoethanol (80 mmoles) and 4,9-dioxa-1,12-dodecanediamine (20 mmoles) were dissolved in dimethylformamide (DMF) under argon. The solution was treated with a solution of poly(aspartic acid) (10 mmoles) and DMF. The reaction was stirred at room temperature for 1 hour and then 70° C. for 2 hours. The mixture was then cooled and most of the liquid was removed by evaporation under reduced pressure. The oily residue was washed repeatedly with ether and then warm tetrahydrofuran. The product was solidified and recovered by filtration. The crude product was dissolved in water and the pH was adjusted to neutral. The solution was then purified with a BioRad P6-DG desalting gel column (BioRad Laboratories, Richmond, CA, U.S.A.). Fractions containing the amino-functionalized polymer were pooled and lyophilized. The number of amino groups on the polymer was determined by Habeeb's TNBS assay [Anal. Biochem. 14:328–336(1966)] and found to be 22 per mg polymer.

Amino functionalized poly(aspartic acid) (10.7 mg) and SMCC (30 mg) were dissolved in DMF. The reaction was allowed to stir at room temperature for 2 hours. Ice water was added to the mixture and the activated polymer was separated from the mixture with a BioRad 6P-DG gel column. The activated polymer was then allowed to react at room temperature for 3 minutes with the glycated peptide (20 mg)

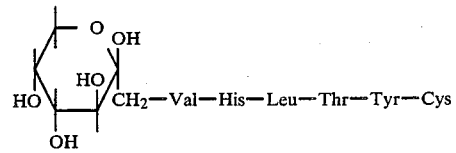

prepared according to the methods described in European Patent Publication No. 185,870. After the reaction, the product was again purified with a 6P-DG gel column and lyophilized.

The number of maleimido groups on the activated polymers was determined by the PDS assay [Grassetti and Murray, Arch. Biochem. Biophys. 119:44–49(1967)] and found to be $0.46\mu$ mole per mg polymer. The amount of Glc-peptide on the polymers was determined by UV/Vis absorption measurement using the molar extinction coefficient at 275 nm for tyrosine and found also to be $0.46\mu$ mole per mg polymer.

2. ASSAY PROCEDURE FOR DETERMINATION OF % HbAlc

A. Reagents:

Ab-Latex

The concentrated Ab-Latex is diluted to the appropriate concentration with 200 mM glycine buffer, pH 9 containing 0.05% BSA-pf and 0.1% sodium azide. Mannitol at a 4% concentration may also be present in the buffer. Following dilution, the Ab-latex solution is sonicated briefly (5 to 10 sec.)

Agglutinator

A working solution of the agglutinator reagent is prepared from a 1.0 mg/mL water stock solution. A 10 μg/mL solution is prepared by diluting the stock with 20 mM phosphate buffer, pH 6 containing 0.1% BSA-pf and 0.1% sodium azide.

Blood-based Calibrators and Clinical Samples

Blood-based calibrator and blood samples must be denatured before use. For use in the assay, blood samples are well mixed by a rocker mixer such as the Ames Aliquot mixer (Miles Inc., Elkhart, IN U.S.A.). These samples are then diluted 1:31 with denaturant/oxidant (3M $NH_4SCN$, 2 mg/mL $K_3Fe(CN)_6$, 10 mM Tris, pH 7.5). The presence of the ferricyanide in the denaturant allows the diluted sample or calibrator to be used for the determination of the hemoglobin concentration. The samples are allowed to sit at least 15 seconds before assaying on the OPTIMATE ™ Instrument (Miles Inc., Elkhart, IN U.S.A.) to allow for complete denaturation of the protein and oxidation of the heme.

B. Turbidimetric Assay for HbAlc

Three different procedures for the OPTIMATE instrument have been used for determination of HbAlc. Two are endpoint formats; one requiring the manual addition of the agglutinator solution and the other completely automating the assay. The third assay format is a rate assay. The following description briefly explains the general format of the three assays.

Endpoint Assay With Manual Addition of Agglutinator

1. Using Chemistry 37—Program New Test, the following assay parameters are programmed as USER CHEMISTRY #25.
   Units—None
   Test Type—Endpoint
   Decimal Places—2
   Dispenser Usage—A
   Lag Time A—1200 sec. (the time between dispensing of reagents and absorbance read)
   Equal Time—6 sec. (the time sample is held in the cuvette before absorbance read)
   Read Time—5 sec. (time over which data is collected, absorbance is read 7.7 times/sec.)
   Cuvette Temp—25° C.
   Standard Conc.—None
   Factor—1000 (factor by which result is multiplied, converts to milliabsorbance units)
   Low I/A (Abs)—2.000 (setting both the low and high absorbance limits to 2.00 forces the
   High I/A (Abs)—2.000 OPTIMATE to print the actual absorbance readings for each sample)
   Low Normal—None
   High Normal—None
   Absorbance Filter—540 nm
   Transport Temp—Room Temperature
   Sample Volume—10 $\mu$L
   Reagent Volume—0.5 mL 2. Prior to starting the assay, verify that the pipetter/diluter is equipped with a 100 $\mu$L sample syringe and a 1.0 mL reagent syringe. The turrets of the pipetter/diluter are set to 10% (10 $\mu$L) for the sample syringe and 50% (0.5 mL) for the reagent syringe.

3. Pipette at least 50 $\mu$L of sample into the OPTIMATE sample cups.

4. Prime the pipetter/diluter with the Ab-latex solution.

5. Manually dispense 25 $\mu$L of the agglutinator solution in the OPTIMATE reaction cups using an Eppendorf Repeater Pipette (1.25 mL capacity tip, setting=1). Leave blank cup #60 and any other cups in which the turbidimetric reaction is not to take place. Pipette 25 $\mu$L of buffer (20 mM phosphate, pH 6, 0.1% BSA-pf, 0.1% sodium azide) into these cups.

6. Start Chemistry #25—USER CHEMISTRY #25 following all printed instructions. The OPTIMATE then automatically pipettes and dispenses sample and Ab-latex into the reaction cups and reads the absorbance after 20 minutes.

Endpoint Assay With Automatic Addition of Agglutinator

1. Equip the OPTIMATE with a Gilford Automatic Dispenser with 1.0 mL syringe. The communication cable is connected to port J4 on the back of the OPTIMATE. The use of this external dispenser is enabled by:
   a. Enter Utility 15 followed by the security code 980456.
   b. Enter Utility 50, Check=0, Option 20 The turret of this dispenser is set to 50% (0.5mL).

2. Using Chemistry 37—Program New Test, the following assay parameters are programmed as USER CHEMISTRY #24.
   Units—None
   Test Type—Endpoint
   Decimal places—2
   Dispenser Usage—A and B
   Dispense B from Tower—Yes
   Time from Dispense A to Dispense B—5 sec
   Lag Time A—1200 sec
   Equil Time—6 sec
   Read Time—5 sec
   Cuvette Temp—25° C.
   Standard Conc.—None
   Factor—1000
   Low I/A (Abs)—2.000
   High I/A (Abs)—2.000
   Low Normal—None
   High Normal—None
   Absorbance Filter—540 nm
   Transport Temp—room temperature
   Sample Volume—10 $\mu$L
   Reagent Volume—0.1 mL 3. Prior to starting the assay, verify that the pipetter/diluter is equipped with a 100 $\mu$L sample syringe and a 250 $\mu$L reagent syringe. The turrets of the pipetter/diluter are set to 10% (10 $\mu$L) for the sample syringe and 10% (25 $\mu$L) for the reagent syringe. Also verify that an immunoassay probe is used on the pipetter/diluter.

4. Pipette at least 50 $\mu$L of sample into the OPTIMATE sample cups.

5. Prime the pipetter/diluter with the agglutinator solution.

6. Prime the external dispenser with Ab-latex solution.

7. Start Chemistry #24—USER CHEMISTRY #24 following all printed instructions. The OPTIMATE then automatically pipettes and dispenses sample and agglutinator into the reaction cups, followed by the addition of Ab-latex five seconds later. The absorbance of the reaction is read after 20 minutes.

Rate Assay

1. Equip the OPTIMATE with a Gilford Automatic Dispenser with a 1.0 mL syringe. The communication cable is connected to port J4 on the back of the OPTIMATE. The use of this external dispenser is enabled by:
   a. Enter Utility 15 followed by the security code 980456.
   b. Enter Utility 50, Check=0, Option 20. The turret of the dispenser is set to 50% (0.5 mL).

2. Using Chemistry 37—Program New Test, the following assay parameters are programmed as USER CHEMISTRY #23.
   Units—None
   Test Type—kinetic enzyme
   Decimal Places—2
   Dispenser Usage—A and B
   Dispense B from Tower—Yes
   Time from Disp A to Disp B—5 sec
   Lag Time A—20 sec
   Equil Time—5 sec
   Read Time—30 sec
   Cuvette Temp.—30° C.
   Standard Conc—None
   Factor—1000
   Low I/A (Abs)—2.000
   High I/A (Abs)—2.000
   Absorbance Filter—540 nm
   Transport Temp—30° C.
   Sample Volume—10 $\mu$L
   Reagent Volume—0.1 mL 3. Prior to starting the assay, verify that the pipetter/diluter is equipped with a 100 $\mu$L sample syringe and a 250 μL reagent syringe. The turrets of the pipetter/diluter are set to 10% (10 μL) for the sample syringe and 10% (25 μL) for the reagent syringe. Also verify that an immunoassay probe is used on the pipetter/diluter.

4. Pipette at least 50 μL of sample into the OPTIMATE sample cups.

5. Prime the pipetter/diluter with the agglutinator solution.

6. Prime the external dispenser with Ab-latex solution.

7. Start Chemistry #23—USER CHEMISTRY #23 following all printer instructions. The OPTIMATE then automatically pipettes and dispenses sample and agglutinator into the reaction cups, followed by the addition of Ab-latex five seconds later. The absorbance of this reaction is read after the 14-second lag period. The absorbance is read for a total of 30 seconds. The OPTIMATE determines the linear regression line through the data it has collected and presents the data in terms of the change in absorbance per minute.

Hemoglobin Determination

For all blood samples, the concentration of hemoglobin in the sample must be determined in order to calculate the percent of HbAlc in the sample. The same denatured sample used for the determination of HbAlc is used for the hemoglobin determination using the following protocol.

1. Using Chemistry 37—Program New Test, the following assay parameters are programmed as USER CHEMISTRY #26.

Units—None
Test Type—Endpoint
Decimal Places—2
Dispenser Usage—A
Lag Time A—300 sec
Equal Time—6 sec
Read Time—5 sec
Cuvette Temp.—25° C.
Standard Conc—None
Factor—1000
Low I/A (Abs)—2.000
High I/A (Abs)—2.000
Low Normal—None
High Normal—None
Absorbance Filter—540 nm
Transport Temp—Room Temperature
Sample Volume—70 μL
Reagent Volume—0.5 mL 2. Prior to starting the assay, verify that the pipetter/diluter is equipped with a 100 μL sample syringe and a 1.0 mL reagent syringe. The turrets of the pipetter/diluter are set to 70% (70 μL) for the sample syringe and 50% (0.5 mL) for the reagent syringe.

3. Pipette at least 120 μL of sample into the OPTIMATE sample cups.

4. Prime the pipetter/diluter with 200 mM glycine, pH 9 buffer containing 0.05% BSA-pf and 0.1% sodium azide.

5. Start Chemistry #26—USER CHEMISTRY #26 following all printed instructions. The OPTIMATE then automatically pipettes and dispenses sample and buffer into the reaction cups and reads the absorbance after five minutes.

Calculations

A number of calculations must be performed in order to transform the information provided by the OPTIMATE into a % HbAlc result.

1. A latex blank reaction (500 μL latex+35 μL buffer) is included in every assay run. The absorbance of this reaction must be subtracted from every other result.

2. For all blood samples, the contribution of the absorbance of hemoglobin to the reaction is calculated using the information collected from USER CHEMISTRY #26. The absorbance result obtained there is divided by seven to calculate the absorbance of 10 μL of blood. This value is then subtracted from the absorbance result obtained above.

3. In order to calculate a standard curve, a dummy immunoassay is programmed using Immunoassay #37—Program New Test. The following parameters are programmed as USER IMMUNOASSAY #27.

Protocol—#1
Calibrator Values—enter the assigned calibrator values for the Glc-peptide calibrators (in terms of μM HbAlc). These are dependent on the lot of Ab-latex used. The values of all other parameters are unimportant but must be entered in order to store the calibrator values.

4. A four parameter logit standard curve is generated using Immunoassay #33—Immunoassay Calculations.

Test #—#27
Calc Scheme—1. 4 Param Logit
Enter Absorbance results (minus latex blank) for the Glc-peptide calibrators.
The OPTIMATE then generates the standard curve, calculating the standard deviation of the curve and the four parameters. Once completed, calculate HbAlc of the unknown samples by entering the absorbance (-ltx blank, -Hb contrib) for all samples. The result printed is the μM HbAlc concentration.

5. The concentration of hemoglobin in each of the blood samples is calculated using the information from USER CHEMISTRY #26. The concentration of hemoglobin is first calculated in terms of g/dL and then this information is used to determine the mM concentration of hemoglobin $\beta$ chains present.

$$\text{Hb (g/dL)} = \frac{\text{Abs. from CHEM \#26} \times 16114.5 \times 252}{9.79 \times 1.0 \times 10{,}000}$$

where
16114.5=MW of one Hb subunit
252=dilution factor
9.79=quarter millimolar extinction coefficient
10,000=correction for unit conversion
Conc of hemoglobin in mM beta subunits:

$$\text{mM beta-Hb Subunits} = \frac{\text{g/dL Hb} \times 10}{64{,}456} \times 1000 \times 2$$

where
10=conversion factor to g/L
64,456=MW of hemoglobin (four subunits)
1000=conversion factor to mM
2=conversion factor for Hb to beta-Hb 6. Now that the μM $HbA_{1c}$ concentration and the hemoglobin concentration (both in terms of the beta subunits) are known, the % $HbA_{1c}$ can be determined.

3. CLINICAL STUDY

Clinical samples (71) were obtained from a local clinical laboratory which had assayed the samples by the conventional HbAlc affinity chromatography method (Isolab, Akron, OH, U.S.A.). The samples were assayed as above using the present invention. The correlation is presented in the drawing.

4. EFFECT OF VARIOUS OXIDANTS ON RATE OF DENATURATION

Different oxidants (in 20 molar excess to the heme concentration of the blood based material in the denaturation mixture) were mixed with 3M NH$_4$SCN in 10 mM Tris, pH=7.5 buffer. The mixture was used to denature the blood samples according to the procedure described in the Sample Preparation Section above. After the addition of the blood samples and at different time intervals, the immuno-reactivity of the samples was examined by the turbidimetric assay for HbAlc assay described in the previous sections. The minimum times required to generate the most (and also constant) immuno-reactivity were determined. The results are shown in Table 1.

The present invention has been particularly described and exemplified above. Obviously, many other variations and modifications of the invention can be made without departing from the spirit and scope thereof.

TABLE 1

Effect of Oxidants on the Denaturation of Hemoglobin

| Denaturant | Oxidant* | Time for complete denaturation(min, RT) |
|---|---|---|
| 3M NH$_4$SCN | none | 7 |
| 3M KSCN | none | 7 |
| 3M NH$_4$SCN | K$_3$Fe(CN)$_6$ | <1 |
| 2M NH$_4$SCN | K$_3$Fe(CN)$_6$ | 7.5 |
| 1.5M NH$_4$SCN | K$_3$Fe(CN)$_6$ | 20 |
| 1.5M NH$_4$SCN | K$_3$Fe(CN)$_6$** | 20 |
| 1.5M NH$_4$SCN | K$_3$Fe(CN)$_6$ | 5*** |
| 3M NH$_4$SCN | KIO$_3$ | 5 |
| 3M NH$_4$SCN | KClO$_3$ | 2.5 |
| 3M NH$_4$SCN | K$_2$CrO$_4$ | 4 |
| 3M NH$_4$SCN | NaNO$_2$ | 2.5 |
| 3M NH$_4$SCN | Na$_3$Co(NO$_2$)$_6$ | **** |

*In 20 molar excess to the heme conc. in the assay.
**In 200 molar excess.
***37° C.
****Interferes with immunoassay.

What is claimed is:

1. An analytical method for determining the relative amount of a particular hemoglobin derivative in a blood sample, comprising the steps of:
    (a) treating the blood sample with (i) a thiocyanate salt capable of denaturing substantially all hemoglobin present in the sample and (ii) an oxidant capable of converting substantially all hemoglobin present in the sample to the met-hemoglobin form,
    (b) assaying the denatured, oxidized blood sample for the amount of total met-hemoglobin present therein which represents the amount of total hemoglobin in the sample,
    (c) assaying the denatured, oxidized blood sample by immunoassay for the amount of the denatured form of said particular hemoglobin derivative present therein, and
    (d) calculating, from the assay results obtained from steps (b) and (c), the relative amount of hemoglobin that is in the form of said particular hemoglobin derivative compared to the total amount of hemoglobin in said blood sample.

2. The method of claim 1 wherein said particular hemoglobin derivative is hemoglobin Alc.

3. The method of claim 1 wherein said oxidant is selected from the group consisting of ferricyanide, chlorate, and nitrite.

4. The method of claim 1 wherein said oxidant is a ferricyanide salt.

5. The method of claim 1 wherein step (a) is performed at room temperature and the concentration of thiocyanate salt is about 3 molar or greater.

6. An analytical method for determining the relative amount of hemoglobin Alc in a blood sample, comprising the steps of:
    (a) combining the blood sample with a denaturant solution comprising a thiocyanate salt and an oxidant capable of converting substantially all forms of hemoglobin present in the sample to their met-hemoglobin forms,
    (b) assaying the denatured, oxidized blood sample for the amount of total met-hemoglobin present therein which represents the amount of total hemoglobin in the sample by measuring absorbance at about 540 nm,
    (c) assaying the denatured, oxidized blood sample for the amount of denatured hemoglobin Alc present therein by an immunoassay based on the specific affinity of a monoclonal antibody reagent for the denatured form of hemoglobin Alc, and
    (d) calculating, from the assay results obtained from steps (b) and (c), the relative amount of hemoglobin that is in the form of hemoglobin Alc compared to the total amount of hemoglobin in said blood sample.

7. The method of claim 6 wherein said oxidant is selected from the group consisting of ferricyanide, chlorate, and nitrite.

8. The method of claim 6 wherein said oxidant is a ferricyanide salt.

9. The method of claim 6 wherein step (a) is performed at room temperature and the concentration of thiocyanate salt in the denaturant solution is about 3 molar or greater.

10. The method of claim 6 wherein said immunoassay is based on particle agglutination inhibition wherein said monoclonal antibody reagent is bound to a water suspensible particle and wherein denatured hemoglobin Alc competes with an agglutinator compound comprising a plurality of epitopic binding sites for said antibody reagent for binding to the reagent particle.

11. The method of claim 6 wherein the met-hemoglobin assay is performed on a first portion of the blood sample and the immunoassay for denatured hemoglobin Alc is performed on a second portion of the sample.

12. The method of claim 6 wherein the met-hemoglobin assay and the immunoassay are performed on the same portion of the treated blood sample or on an aliquot of such sample portion.

13. A test system for determining the relative amount of a particular hemoglobin derivative in a blood sample, comprising:
    (1) a thiocyanate salt capable of denaturing substantially all hemoglobin normally expected to be present in the sample,
    (2) an oxidant capable of converting substantially all forms of hemoglobin normally expected to be present in the blood sample to their met-hemoglobin forms, and (3) reagents for immunoassaying the denatured oxidized blood sample resulting from combining the blood sample with said thiocyanate salt and oxidant for the amount of the denatured oxidized hemoglobin form of said particular hemoglobin derivative present therein.

14. The test system of claim 13 wherein said oxidant is selected from the group consisting of ferricyanide, chlorate, and nitrite.

15. The test system of claim 13 wherein said oxidant is a ferricyanide salt.

16. The test system of claim 13 wherein said particular hemoglobin derivative to be determined is hemoglobin A1c.

17. The test system of claim 16 wherein said oxidant is a ferricyanide salt.

18. The test system of claim 16 wherein the reagents for assaying for denatured hemoglobin A1c comprise a monoclonal antibody reagent specific for the denatured form of hemoglobin A1c.

19. The test system of claim 18 wherein said immunoassay reagents comprise (i) said monoclonal antibody, or a fragment thereof, bound to a water suspensible particle, and (ii) an agglutinator reagent comprising a plurality of epitopic binding sites for said antibody reagent, whereby said immunoassay reagents are capable of assaying denatured hemoglobin A1c by particle agglutination inhibition.

* * * * *